(12) United States Patent
Gertzman et al.

(10) Patent No.: US 7,879,103 B2
(45) Date of Patent: Feb. 1, 2011

(54) VERTEBRAL DISC REPAIR

(75) Inventors: Arthur A. Gertzman, Flemington, NJ (US); Barbara L. Merboth, Bridgewater, NJ (US); Michael Schuler, Princeton, NJ (US); Anton J. Steiner, Wharton, NJ (US); Eric J. Semler, Piscataway, NJ (US); Judith I. Yannariello-Brown, Somerset, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 28 days.

(21) Appl. No.: 11/404,806

(22) Filed: Apr. 17, 2006

(65) Prior Publication Data

US 2006/0235534 A1  Oct. 19, 2006

Related U.S. Application Data

(60) Provisional application No. 60/671,514, filed on Apr. 15, 2005, provisional application No. 60/791,904, filed on Apr. 14, 2006.

(51) Int. Cl.
*A61F 2/44* (2006.01)

(52) U.S. Cl. .................. 623/17.16; 623/23.51; 623/919; 8/94.11

(58) Field of Classification Search ... 623/17.11–17.16, 623/23.51, 23.61, 919; 8/94.11
See application file for complete search history.

(56) References Cited

U.S. PATENT DOCUMENTS

| | | | |
|---|---|---|---|
| 3,867,728 A | 2/1975 | Stubstad et al. | |
| 3,875,595 A | 4/1975 | Froning | |
| 4,349,921 A | 9/1982 | Kuntz | |
| 4,399,814 A | 8/1983 | Pratt et al. | |
| 4,466,435 A | 8/1984 | Murray | |
| 4,488,549 A | 12/1984 | Lee et al. | |
| 4,501,269 A | 2/1985 | Bagby | |
| 4,576,152 A | 3/1986 | Muller et al. | |
| 4,625,722 A | 12/1986 | Murray | |
| 4,655,749 A | 4/1987 | Fischione | |
| 4,655,777 A | 4/1987 | Dunn et al. | |

(Continued)

FOREIGN PATENT DOCUMENTS

DE  29908794 U1  9/1999

(Continued)

OTHER PUBLICATIONS

International Search Report for International Application No. PCT/US2006/14342, filed Apr. 17, 2006.

(Continued)

*Primary Examiner*—Eduardo C Robert
*Assistant Examiner*—Steven J Cotroneo
(74) *Attorney, Agent, or Firm*—Greenberg Traurig, LLP

(57) ABSTRACT

A sterile implant for treatment of a spinal disc defect comprising an allograft cortical bone demineralized to a Type I collagen having a specific shape which is treated to eliminate osteoinductivity. The implant is lyophilized and compressed into smaller first shape which 20 to 80% from its original shape in at least one dimension and hardened. The implant expanding when hydrated into a second shape having the shape memory of the first shape and expanded in dimensional size from the first compressed shape.

45 Claims, 4 Drawing Sheets

U.S. PATENT DOCUMENTS

| | | | |
|---|---|---|---|
| 4,735,625 | A | 4/1988 | Davidson |
| 4,751,921 | A | 6/1988 | Park |
| 4,755,184 | A | 7/1988 | Silverberg |
| 4,772,287 | A | 9/1988 | Ray et al. |
| 4,815,454 | A | 3/1989 | Dozier, Jr. |
| 4,834,757 | A | 5/1989 | Brantigan |
| 4,863,477 | A | 9/1989 | Monson |
| 4,865,604 | A | 9/1989 | Rogozinski |
| 4,904,260 | A | 2/1990 | Ray et al. |
| 4,911,718 | A | 3/1990 | Lee et al. |
| 4,932,969 | A | 6/1990 | Frey et al. |
| 4,932,975 | A | 6/1990 | Main et al. |
| 4,936,848 | A | 6/1990 | Bagby |
| 5,015,255 | A | 5/1991 | Kuslich |
| 5,047,055 | A | 9/1991 | Bao et al. |
| 5,053,049 | A | 10/1991 | Campbell |
| 5,059,193 | A | 10/1991 | Kuslich |
| 5,071,040 | A | 12/1991 | Laptewicz, Jr. |
| 5,108,438 | A | 4/1992 | Stone |
| 5,171,280 | A | 12/1992 | Baumbgartner |
| 5,171,281 | A | 12/1992 | Parsons et al. |
| 5,181,918 | A | 1/1993 | Brandhorst et al. |
| 5,192,325 | A | 3/1993 | Kijima et al. |
| 5,192,326 | A | 3/1993 | Bao et al. |
| 5,192,327 | A | 3/1993 | Brantigan |
| 5,282,863 | A | 2/1994 | Burton |
| 5,298,254 | A | 3/1994 | Prewett et al. |
| 5,303,718 | A | 4/1994 | Krajicek |
| 5,306,307 | A | 4/1994 | Senter et al. |
| 5,306,308 | A | 4/1994 | Gross et al. |
| 5,306,309 | A | 4/1994 | Wagner et al. |
| 5,306,310 | A | 4/1994 | Seibels |
| 5,306,311 | A | 4/1994 | Stone et al. |
| 5,314,476 | A | 5/1994 | Prewett et al. |
| 5,314,477 | A | 5/1994 | Marnay |
| 5,314,478 | A | 5/1994 | Oka et al. |
| 5,324,273 | A | 6/1994 | Discko, Jr. |
| 5,431,654 | A | 7/1995 | Nic |
| 5,439,684 | A | 8/1995 | Prewett et al. |
| 5,443,514 | A | 8/1995 | Steffee |
| 5,501,687 | A | 3/1996 | Willert et al. |
| 5,507,813 | A | 4/1996 | Dowd et al. |
| 5,545,222 | A | 8/1996 | Bonutti |
| 5,549,679 | A | 8/1996 | Kuslich |
| 5,571,189 | A | 11/1996 | Kuslich |
| 5,577,517 | A | 11/1996 | Bonutti |
| 5,658,341 | A | 8/1997 | Delfosse |
| 5,697,932 | A | 12/1997 | Smith et al. |
| 5,702,454 | A | 12/1997 | Baumgartner |
| 5,711,957 | A | 1/1998 | Patat et al. |
| 5,718,707 | A | 2/1998 | Mikhail |
| 5,755,797 | A | 5/1998 | Baumgartner |
| 5,782,919 | A | 7/1998 | Zdeblick et al. |
| 5,814,084 | A | 9/1998 | Grivas et al. |
| 5,824,087 | A | 10/1998 | Aspden et al. |
| 5,842,786 | A | 12/1998 | Solomon |
| 5,863,297 | A | 1/1999 | Walter et al. |
| 5,899,939 | A | 5/1999 | Boyce et al. |
| 5,910,315 | A | 6/1999 | Stevenson et al. |
| 5,972,368 | A | 10/1999 | McKay |
| 5,989,289 | A | 11/1999 | Coates et al. |
| 5,997,581 | A | 12/1999 | Khalili |
| 5,997,582 | A | 12/1999 | Weiss |
| 6,004,325 | A | 12/1999 | Vargas, III |
| 6,019,765 | A | 2/2000 | Thornhill et al. |
| 6,022,376 | A | 2/2000 | Assell et al. |
| 6,025,538 | A | 2/2000 | Yaccarino, III |
| 6,027,743 | A | 2/2000 | Khouri et al. |
| 6,039,762 | A | 3/2000 | McKay |
| 6,090,998 | A | 7/2000 | Grooms et al. |
| 6,096,081 | A | 8/2000 | Grivas et al. |
| 6,123,731 | A | 9/2000 | Boyce |
| 6,132,465 | A * | 10/2000 | Ray et al. ............... 623/17.16 |
| 6,183,518 | B1 | 2/2001 | Ross et al. |
| 6,200,347 | B1 | 3/2001 | Anderson et al. |
| 6,224,630 | B1 | 5/2001 | Bao et al. |
| 6,240,926 | B1 | 6/2001 | Chin Gan et al. |
| 6,245,107 | B1 | 6/2001 | Ferree |
| 6,261,586 | B1 | 7/2001 | McKay |
| 6,270,528 | B1 | 8/2001 | McKay |
| 6,294,187 | B1 | 9/2001 | Boyce et al. |
| 6,379,385 | B1 | 4/2002 | Kalas et al. |
| 6,383,211 | B1 | 5/2002 | Staehle |
| 6,395,034 | B1 | 5/2002 | Suddaby |
| 6,398,811 | B1 | 6/2002 | McKay |
| 6,419,707 | B1 | 7/2002 | Leclercq |
| 6,432,436 | B1 * | 8/2002 | Gertzman et al. ............ 424/423 |
| 6,437,018 | B1 | 8/2002 | Gertzman et al. |
| 6,443,988 | B2 | 9/2002 | Felt et al. |
| 6,447,514 | B1 | 9/2002 | Stalcup et al. |
| 6,458,144 | B1 | 10/2002 | Morris et al. |
| 6,458,158 | B1 | 10/2002 | Anderson et al. |
| 6,554,803 | B1 | 4/2003 | Ashman |
| 6,599,293 | B2 | 7/2003 | Tague et al. |
| 6,620,162 | B2 | 9/2003 | Kuslich et al. |
| 6,620,169 | B1 | 9/2003 | Peterson et al. |
| 6,620,196 | B1 | 9/2003 | Trieu |
| 6,626,912 | B2 | 9/2003 | Speitling |
| 6,632,247 | B2 * | 10/2003 | Boyer et al. ............... 623/23.6 |
| 6,645,213 | B2 | 11/2003 | Sand et al. |
| 6,652,593 | B2 | 11/2003 | Boyer, II et al. |
| 6,676,664 | B1 | 1/2004 | Al-Assir |
| 6,692,528 | B2 * | 2/2004 | Ward et al. ............... 623/17.12 |
| 6,696,073 | B2 | 2/2004 | Boyce et al. |
| 6,712,853 | B2 | 3/2004 | Kuslich |
| 6,758,863 | B2 | 7/2004 | Estes et al. |
| 6,761,739 | B2 | 7/2004 | Shepard |
| 6,767,369 | B2 | 7/2004 | Boyer et al. |
| 6,783,546 | B2 | 8/2004 | Zucherman et al. |
| 6,855,167 | B2 | 2/2005 | Shimp et al. |
| 6,902,578 | B1 | 6/2005 | Anderson et al. |
| 6,984,247 | B2 | 1/2006 | Cauthen |
| 6,991,653 | B2 | 1/2006 | White et al. |
| 7,025,771 | B2 | 4/2006 | Kuslich et al. |
| 7,044,968 | B1 | 5/2006 | Yaccarino, III et al. |
| 7,048,762 | B1 | 5/2006 | Sander et al. |
| 7,048,765 | B1 | 5/2006 | Grooms et al. |
| 7,056,345 | B2 | 6/2006 | Kuslich |
| 7,087,082 | B2 | 8/2006 | Paul et al. |
| 7,094,258 | B2 | 8/2006 | Lambrecht et al. |
| 7,115,146 | B2 | 10/2006 | Boyer et al. |
| 7,179,299 | B2 | 2/2007 | Edwards et al. |
| 7,220,282 | B2 | 5/2007 | Kuslich |
| 7,226,481 | B2 | 6/2007 | Kuslich |
| 7,226,482 | B2 | 6/2007 | Messerli et al. |
| 7,309,359 | B2 | 12/2007 | Trieu et al. |
| 7,323,011 | B2 | 1/2008 | Shepard et al. |
| 7,479,160 | B2 | 1/2009 | Branch et al. |
| 7,537,617 | B2 | 5/2009 | Bindsell et al. |
| 7,563,455 | B2 | 7/2009 | McKay |
| 7,601,173 | B2 | 10/2009 | Messerli et al. |
| 7,608,113 | B2 | 10/2009 | Boyer et al. |
| 2001/0020188 | A1 | 9/2001 | Sander |
| 2001/0031254 | A1 | 10/2001 | Bianchi et al. |
| 2001/0039457 | A1 | 11/2001 | Boyer, II et al. |
| 2001/0041941 | A1 | 11/2001 | Boyer, II et al. |
| 2001/0043940 | A1 | 11/2001 | Boyce et al. |
| 2001/0339458 | | 11/2001 | Boyer, II et al. |
| 2002/0013600 | A1 | 1/2002 | Scribner et al. |
| 2002/0016592 | A1 | 2/2002 | Branch et al. |
| 2002/0026195 | A1 | 2/2002 | Layne et al. |
| 2002/0035401 | A1 | 3/2002 | Boyce et al. |
| 2002/0045942 | A1 | 4/2002 | Ham |
| 2002/0068974 | A1 | 6/2002 | Kuslich |

| | | | |
|---|---|---|---|
| 2002/0077701 A1 | 6/2002 | Kuslich | |
| 2002/0106393 A1 | 8/2002 | Bianchi et al. | |
| 2002/0138143 A1 | 9/2002 | Grooms et al. | |
| 2002/0147496 A1 | 10/2002 | Belef et al. | |
| 2002/0156531 A1 | 10/2002 | Felt et al. | |
| 2003/0023311 A1* | 1/2003 | Trieu | 623/17.16 |
| 2003/0093154 A1* | 5/2003 | Estes et al. | 623/17.11 |
| 2003/0144743 A1 | 7/2003 | Edwards et al. | |
| 2004/0006348 A1 | 1/2004 | Peterson et al. | |
| 2004/0054414 A1* | 3/2004 | Trieu et al. | 623/17.16 |
| 2004/0073314 A1 | 4/2004 | White et al. | |
| 2004/0102850 A1 | 5/2004 | Shepard | |
| 2004/0115172 A1 | 6/2004 | Bianchi et al. | |
| 2004/0138748 A1 | 7/2004 | Boyer, II et al. | |
| 2004/0143344 A1 | 7/2004 | Malaviya et al. | |
| 2004/0215201 A1 | 10/2004 | Lieberman | |
| 2004/0215343 A1 | 10/2004 | Hochschuler et al. | |
| 2004/0225296 A1 | 11/2004 | Reiss et al. | |
| 2004/0243242 A1 | 12/2004 | Sybert et al. | |
| 2005/0004672 A1 | 1/2005 | Pafford et al. | |
| 2005/0043808 A1 | 2/2005 | Felt et al. | |
| 2005/0055094 A1 | 3/2005 | Kuslich | |
| 2005/0065609 A1 | 3/2005 | Wardlaw | |
| 2005/0119754 A1 | 6/2005 | Trieu et al. | |
| 2005/0125077 A1 | 6/2005 | Harmon et al. | |
| 2005/0131417 A1 | 6/2005 | Ahern et al. | |
| 2005/0197707 A1 | 9/2005 | Trieu et al. | |
| 2005/0209602 A1 | 9/2005 | Bowman et al. | |
| 2005/0228498 A1 | 10/2005 | Andres | |
| 2005/0261681 A9 | 11/2005 | Branch et al. | |
| 2005/0261767 A1 | 11/2005 | Anderson et al. | |
| 2006/0030948 A1 | 2/2006 | Manrique et al. | |
| 2006/0149379 A1 | 7/2006 | Kuslich et al. | |
| 2006/0195193 A1 | 8/2006 | Bloemer et al. | |
| 2006/0235534 A1 | 10/2006 | Gertzman et al. | |
| 2006/0276907 A1 | 12/2006 | Boyer, II et al. | |
| 2007/0016214 A1 | 1/2007 | Kuslich et al. | |
| 2007/0067040 A1 | 3/2007 | Ferree | |
| 2007/0093912 A1 | 4/2007 | Borden | |
| 2007/0100450 A1 | 5/2007 | Hodorek | |
| 2007/0134291 A1 | 6/2007 | Ting | |
| 2007/0168030 A1 | 7/2007 | Edwards et al. | |
| 2007/0260324 A1 | 11/2007 | Joshi et al. | |
| 2008/0015709 A1 | 1/2008 | Evans et al. | |
| 2008/0027546 A1* | 1/2008 | Semler et al. | 623/17.11 |
| 2008/0045952 A1 | 2/2008 | Kuslich | |
| 2008/0113008 A1 | 5/2008 | Roche | |
| 2008/0305145 A1 | 12/2008 | Shelby et al. | |
| 2009/0099661 A1 | 4/2009 | Bhattacharya et al. | |
| 2009/0131986 A1 | 5/2009 | Lee et al. | |
| 2009/0297580 A1 | 12/2009 | Dony et al. | |

FOREIGN PATENT DOCUMENTS

| | | |
|---|---|---|
| EP | 0277282 B1 | 6/1991 |
| EP | 0322334 B1 | 2/1992 |
| EP | 0517030 A2 | 12/1992 |
| EP | 0621020 A1 | 10/1994 |
| EP | 0517030 B1 | 9/1996 |
| EP | 1868539 A2 | 12/2007 |
| EP | 2076220 A2 | 7/2009 |
| FR | 2639823 A1 | 8/1990 |
| FR | 2662073 A1 | 11/1991 |
| GB | 2262238 A | 6/1993 |
| WO | WO 93/16664 A1 | 9/1993 |
| WO | WO 94/20047 A1 | 9/1994 |
| WO | WO 99/08616 A1 | 2/1999 |
| WO | 99/09914 A1 | 3/1999 |
| WO | 00/28907 A1 | 5/2000 |
| WO | WO 00/28907 A1 | 5/2000 |
| WO | 00/40177 A1 | 7/2000 |
| WO | 02/064180 A1 | 8/2002 |
| WO | WO 2006/113586 A2 | 10/2006 |
| WO | WO 2006/113586 A3 | 9/2007 |
| WO | WO 2008/013763 A2 | 1/2008 |
| WO | WO 2008/013763 A3 | 6/2008 |

OTHER PUBLICATIONS

International Preliminary Report on Patentability Containing the Written Opinion of the International Searching Authority for PCT/US2006/14342.

International Search Report mailed on Jul. 24, 2007 in connection with International Patent Application No. PCT/US2006/014342.

Written Opinion mailed on Jul. 24, 2007 in connection with International Patent Application No. PCT/US2006/014342.

International Preliminary Report on Patentability mailed on Oct. 16, 2007 in connection with International Patent Application No. PCT/US2006/014342.

International Search Report mailed on Apr. 29, 2008 in connection with International Patent Application No. PCT/US2007/016528.

Written Opinion mailed on Apr. 29, 2008 in connection with International Patent Application No. PCT/US2007/016528.

International Preliminary Report on Patentability mailed on Jan. 27, 2009 in connection with International Patent Application No. PCT/US2007/016528.

Canadian Office Action mailed on Jul. 20, 2009 in connection with Canadian Patent Application No. 2,604,622.

Australian Office Action mailed Feb. 6, 2009 in connection with Australian Patent Application No. 2006236548.

Kuslich et al., "The Origin of Low Back Pain and Sciatics: A Microsurgical Investigation," reprinted from *Microsurgery of the Lumbar Spine*, R. W. Williams et al. (Eds.) pp. 1-7 (1990).

Kuslich, "Microsurgical Nerve Root Decompression Utilizing Progressive Local Anesthesia," reprinted from *Microsurgery of the Lumbar Spine*, R.W. Williams et al. (Eds.) pp. 139-147 (1990).

Kadoya, MD, et al., "Biomechangical and Morphologic Evaluation of a Three-Dimensional Fabric Sheep Artificial Intervertebral Disc; In Vitro and In Vivo Analysis," SPINE vol. 26, No. 14, 1562-1569 (2001).

Meakin et al., "Effect of removing the nucleus pulposus on the deformation of the annulus fibrosus during compression of the intervertebral disc", Journal of Biomechanics, vol. 33, (2000), pp. 575-580.

Office Action mailed May 19, 2010 in connection with U.S. Appl. No. 11/878,269.

Non-final Office Action mailed on May 19, 2010 in connection with U.S. Appl. No. 11/878,269.

Office Action mailed on May 31, 2010 in connection with Canadian Patent Application No. 2,604,622.

* cited by examiner

VERTEBRAL DISC REPAIR

RELATED APPLICATIONS

This is an application claiming priority from U.S. Provisional Application No. 60/671,514 filed Apr. 15, 2005 and U.S. Provisional Application No. 60/791,904, filed Apr. 14, 2006.

FIELD OF INVENTION

The present invention is directed toward a shaped implant constructed of Type I collagen obtained from demineralized bone which is used for human spinal disc repair. The Type I collagen is treated to eliminate osteoinductivity and the implant is used to replace or augment the nucleus pulposus of a degenerated spinal disc after rupture or herniation. More specifically, the present invention is directed to a load-bearing implant which possesses a unique advantage of shape-memory.

BACKGROUND OF THE INVENTION

Degeneration of the intervertebral disc within the spine is generally believed to be a common cause of debilitating lower back and neck pain. An intervertebral disc primarily serves as a mechanical cushion between the vertebral bones, permitting controlled motions within vertebral segments of the axial skeleton. The normal disc is a unique, structure, comprised of three component tissues: the nucleus pulposus ("NP"), the annulus fibrosus ("AF"), and the cartilaginous end plates of the two opposing vertebral bodies. The configuration of the healthy disc is such that the NP, a soft gelatinous material, is situated in the center of the disc while the AF, a tough, laminated ring of crisscrossing layers, surrounds and contains the NP. The disc is connected to the superior and inferior vertebrae through hyaline cartilage-based vertebral end plates that are approximately 1 mm thick and serve as a semipermeable membrane.

The AF is a tough annular shaped fibrocartilage tissue which consists mainly of Type 1 collagen fibers which are organized into many crisscrossed layers forming a tough, outer fibrous ring that binds together adjacent vertebrae. Approximately 60-70% of the mass of the AF is water. This fibrous portion, which is shaped much like a laminated automobile tire, is generally about 10 to 15 millimeters in height and about 15 to 20 millimeters in thickness. The AF consists of overlapping multiple plies at roughly a 30-degree angle with respect to the radial direction that are sequentially oriented to alternate in direction. The fibers of the AF are connected to the vertebral end plates as well as being directly bound to the superior and inferior vertebral bodies. This configuration particularly resists torsion, as about half of the angulated fibers will tighten when the vertebrae rotate in either direction, relative to each other. The laminated plies are less firmly attached to each other. This configuration ensures significant resistance against radial stress and inner overpressure, while allowing significant deformation during twisting and bending.

The AF disc contains a complex flexible and hydrophilic core, the nucleus pulposus (NP). The NP consists of a gel-like composite made of proteoglycans (PGs) and Type II collagen. The NP resides in the center of the AF and the transition between these two tissues is quite distinct at birth but becomes more gradual with increasing age. The high PGs content, as much as 65% for young individuals allows it to maintain a water content of more than 90% of its total mass. PGs possess glycosaminoglycan chains with ionic carbonyl and sulfate groups that have the ability to attract and retain water molecules. The NP absorbs water rapidly when load is applied to the spine (sitting up, standing, hip rotation, walking, etc.) serving as a pump that takes up and expels water depending on the pressure within the disc. In this manner, the degree to which the disc is loaded with external forces determines the amount of water in the NP. For example, if the disc is under increased compression, the pressure within the disc increases and water is forced out of the NP. When the load on the disc decreases, the pressure within the disc lessens and water is allowed to flow back in. This phenomenon is an effective mechanism for providing the exchange of waste and nutrients through the vertebral end plates. This is particularly critical for cells that reside within the disc since the disc is a largely avascular structure, having no direct blood supply. A healthy NP is largely a gel-like substance having a high water content, and similar to the air in a tire, serves to keep the annulus tight in tension yet flexible enough to allow some degree of motion.

The complex structure of the intervertebral disc performs the important role of absorbing mechanical loads while allowing for constrained flexibility of the spine. A healthy NP is critical to the disc function and the normal load transfer mechanism that occurs within the spine. In particular, the swelling pressure generated by the NP transmits external forces that act on the disc to the AF. For example, an axial load acting on the disc causes the intradiscal pressure within the NP to increase thereby creating tension on the surrounding ring shaped AF, pushing it outward and preventing it from bulging inward. When the fibers of the AF are stretched, they are strengthened to better resist the vertical loading on the disc.

With increased aging, degenerative changes naturally occur within the disc. The term, degenerative disc disease (DDD), refers to degradation of normal disc architecture into a pathological state. It has been previously reported that by age 50, nearly all intervertebral discs have undergone some degree of degeneration. The onset of DDD is believed to occur as the NP begins to lose its ability to retain water. This is due to a decrease in the PGs content within the NP of the disc as well as changed in the PGs chemical composition. More specifically, the PGs composition is modified as the ratio of keratin sulfate to chondroitin sulfate increases. The changes result in the PGs composing approximately 65% of the dry weight of the NP in young individuals to less than 30% with aging. This impacts the water binding capacity of the NP as its water content may decline from about 90% at birth to about 70% or less in old age. There is also an associated decrease in the number of resident cells within the NP tissue. With the decreased water content and cellularity, the NP loses volume and becomes less gel-like and more fibrous in nature and the border between the NP and the AF becomes much less distinct. This transformation of the NP within the disc is similar to the air leaking from a tire.

As the DDD evolves, the load transfer mechanism of the disc is significantly modified. With these pathologic changes, the NP can no longer effectively transfer loads and provide sufficient pressurization to keep the AF in tension. When not properly tensioned, the layers of the AF do not have the same ability to resist compressive loads and experience atypical stresses. Without a healthy NP to resist the AF from bulging inward, this abnormal stretching of the AF causes this tissue structure to weaken by making the successive plies buckle and separate from each other. This causes the AF to become more susceptible to radial fissures or cracks under loading.

Over time, the disc also loses stability and height bringing the spinal facet joints in close contact with each other.

Following a full-thickness tear in the AF, the NP is no longer prevented from escaping from the disc under loading. NP material then moves through the crack in the annulus and reaches the outside of the disc where it may cause inflammation and come into contact with a nerve root. This phenomenon is often referred to as "herniated" disc with the nerve impingement typically resulting in debilitating back or leg pain, loss of muscle control or even paralysis. The most common resulting symptoms are pain radiating along a compressed nerve and low back pain, either of which can be crippling for the patient. The significance of this problem is increased by the low average age of diagnosis with over 80% of patients in the United States being under 59.

While conservative care is frequently the first treatment option, surgical solutions are often necessary to alleviate pain and discomfort. When conservative approaches are not successful, the most common surgical options are currently discectomy and spinal fusion. While both of these options are reasonably successful at acutely decreasing pain, neither one restores proper biomechanics to the spine, which may lead to further degeneration at the operated disc or discs at the adjacent levels in the spine.

Since 1934, discectomy has been utilized as a common surgical procedure for treating intervertebral disc herniation. This procedure is performed with the AF still relatively intact and involves removal of disc materials impinging on the nerve roots or spinal cord external to the disc, generally posteriorly. Depending on the surgeon's preference, varying amounts of NP are then removed from within the disc space either through the herniation site or through an incision in the AF. This removal of extra NP further diminishes the volume of the NP but is commonly done to minimize the risk of recurrent herniation.

The most significant drawbacks of discectomy are recurrence of herniation, recurrence of radicular symptoms, continuing loss of disc height and increasing low back pain. Re-herniation can occur in a significant number of cases. The site for re-herniation is most commonly the same level and side as the previous herniation and can occur through the same weakened site in the AF. Persistence or recurrence of radicular symptoms happens in many patients and when not related to re-herniation, tends to be linked to stenosis of the neural foramina caused by a loss in height of the operated disc. All of these failings are most directly related to the loss of NP material and AF competence that results from herniation and surgery.

Loss of NP material via discectomy further deflates the disc, causing a decrease in disc height. Loss of disc height increases loading on the facet joints. This can result in deterioration of facet cartilage and ultimately osteoarthritis and pain in this joint. As the joint space decreases the neural foramina formed by the inferior and superior vertebral pedicles also close down. This leads to foraminal stenosis, pinching of the traversing nerve root, and recurring radicular pain. Loss of NP also increases loading on the remaining AF, a partially ennervated structure that can produce pain. Finally, loss of NP results in greater bulging of the AF under load. This can result in renewed impingement by the AF on nerve structures posterior to the disc.

Persisting tears in the AF that result either from herniation or surgical incision also contribute to poor results from discectomy. The AF has limited healing capacity with the greatest healing occurring in its outer borders. Healing takes the form of a thin fibrous film that does not approach the strength of the uninjured disc. Surgical incision in the AF has been shown to produce immediate and long lasting decreases in stiffness of the AF particularly against torsional loads. This may over-stress the facets and contribute to their deterioration. Further, in as many as 30% of cases, the AF never closes. In these cases, not only is re-herniation a risk but also leakage of fluids or solids from within the NP into the epidural space can occur. This has been shown to cause localized pain, irritation of spinal nerve roots, decreases in nerve conduction velocity, and may contribute to the formation of post-surgical scar tissue in the epidural space.

Spinal fusion is a common surgical treatment option for patients that have persistent back pain and whose annulus is severely compromised. This procedure involves removing a majority of the disc and causing bone to grow between the two adjacent vertebrae. If successful, this results in the two vertebrae being "fused" together This treatment generally reduces back pain but limits the mobility of the spine. It is suspected that this abnormal biomechanical loading may lead to DDD and repeat surgeries at the adjacent levels.

All present surgical interventions, whether laminectomy or fusion of adjacent vertebrae, lower the functionality of the spine in some way. For that reason it is desirable to try to develop a prosthetic for the spinal disc or its parts. This is, however, extremely difficult. The spine is a very complex part of the body and its proper function is dependent on proper coordination of the function of all the parts, including the spinal discs. The spinal disc needs to withstand complex stresses, including various angles of bending, pressure, shear, and twisting. The spinal disc must also function as a shock and vibration absorber. And finally, a spinal disc must allow the transport of the nutrients and metabolic products needed for its health and survival.

There have been a number of attempts to try to correct or repair the problems connected to defective spinal discs. The first prostheses embodied a wide variety of ideas primarily using mechanical devices such as ball bearings, springs, metal spikes and other perceived aids. These prosthetic discs were designed to replace the entire intervertebral disc space, and were large and rigid. Beyond the questionable efficacy of those devices were the inherent difficulties encountered during implantation.

A new procedure has been developed which is a mechanical, motion-preserving device replacing the natural interbody joint. The mechanical disc is based on the highly successful hip or knee prostheses; these have metal on plastic or metal on metal rotating or sliding elements. These mechanical discs are in the early stages of clinical evaluation and are relatively unproven. Concerns exist based on the metal/plastic interface which would result in fine plastic particles being created in the delicate disc space adjacent to the spinal chord. These plastic debris particles have caused serious complications in the knee and hip applications.

The construction of a fully functional prosthesis is extremely difficult and most prosthetic devices suggested to date are strictly mechanical, and they mimic only some functions of the disc. A prosthetic with a simulation of the disc function is shown in U.S. Pat. No. 4,911,718 issued Mar. 27, 1990 describing a composite construction of the prosthetic of the disc using a biocompatible elastomer, reinforced by fibers which mimic the function of collagen fibers in a natural spinal disc. One disadvantage of this solution, which is common to all full spinal disc replacements, remains a complicated surgical procedure, which translates into a high cost, and a high risk to the patient.

Another surgical approach to restore natural biomechanics in the spine for patients with DDD is augmentation or replacement of the disc nucleus. Here, rather than replacing the entire disc, only the central core of the disc is modified. This preserves the surrounding structures of the disc including the annulus as well as the cartilaginous end plates. The procedure is less complicated and less invasive than TDR therapies. However, this approach does require the AF to be sufficiently intact to contain the NP implant.

The first disc nucleus replacements implant into humans were stainless steel balls developed by Fernstrom in 1966. These solid implants did not restore proper biomechanics in discs due to their stiffness. In addition, some implants migrated from the disc space or subsided into the vertebral end plates.

U.S. Pat. No. 5,047,055 issued Sep. 10, 1991 describes a hydrogel prosthesis of the nucleus, whose shape and size corresponds to the removed disc nucleus when the prosthesis is fully swollen. The prosthetic is prepared in a partially dehydrated state when the dimensions are smaller and the device can be inserted through a smaller opening. After implantation, the prosthesis will grow to its full size by absorbing bodily fluids. It is necessary to note, however, that the dehydration prior to implantation and rehydration after implantation are isotropic, i.e. all dimensions change at the same rate. During implantation the implant will try to expand equally in all directions, but it will expand most in the direction of the least resistance. Therefore it will expand the least in the axial direction, where expansion is most needed (so that the separation of the vertebrae is the highest), and it will expand the most in the radial direction, where the expansion is least desirable; especially in places where the AF is weakened or even missing.

The use of expandable materials in a prosthetic element is also disclosed in U.S. Pat. No. 5,545,222 issued Aug. 13, 1996. Such materials which expand when they come in contact with water or other fluids include PEEK (polyetheretherketone), a desiccated biodegradable material, or a desiccated allograft. As an example, a tendon can be compressed in a desiccated state, and as it imbibes water it expands and creates a firmer lock or tighter fit in the host site.

A shaped, swollen demineralized bone and its use in bone repair is disclosed in U.S. Pat. No. 5,298,254 issued Mar. 29, 1994. In general, cortical allogeneic bone tissue is preferred as the source of bone. Demineralized bone is contacted with a biocompatible swelling agent for a period of time sufficient to cause swelling of the piece.

U.S. Pat. No. 6,620,196 issued Sep. 16, 2003 is directed toward a nucleus pulposus implant having an elastic body and an outer shell which can take a number of forms including a cylinder, rectangular block, spiral and other shapes having a shape memory. The body can be formed from a wide variety of biocompatible polymeric materials.

U.S. Pat. No. 6,652,593 issued Nov. 25, 2003 discloses a demineralized cancellous bone formed into an implant. The implant is capable of being softened and compressed into a small first shape and hardened in the first shape. The compressed shape is hydrated and expands into a second shape having larger dimensions than the original shape. The demineralized cancellous bone may also be used in nucleus replacement.

U.S. Patent Publication No. 2004/0243242 published Dec. 2, 2004 is directed towards an implant constructed of a demineralized fibular ring placed within the medullary canal of another demineralized femoral ring for replacement of an invertebral disc. The disc implant is placed so that the axis of the medullary canal runs parallel to the axis of loading to provide load bearing capacity.

As previously described, in addition to restoring normal biomechanics within the disc, an important feature of a prosthetic nucleus pulposus implant is that the annulus is not entirely removed upon implantation. Normally, however, an opening of some type must be created through the annulus in order for the device to be inserted. Since the creation of this opening traumatizes the annulus, it is highly desirable to minimize its size. Unfortunately, however, most prosthetic nucleus devices that are designed to be implanted through a small annulotomy do not properly fill the nuclear cavity. On the other hand, a relatively rigid prosthesis configured to approximate a shape of the natural nucleus requires an extremely large opening in the annulus in order for the prosthetic device to "pass" into the nucleus cavity.

Degenerated, painfully disabling spinal discs are a major economic and social problem for patients, their families, employers and the public at large. Any significant means to correct these conditions without further destruction or fusion of the disc will serve an important role and be highly beneficial. Other means to replace the function of a degenerated disc have major problems such as complex surgical procedures, unproven efficacy, placing unnecessary and possibly destructive forces on an already damaged annulus, etc. Therefore, a substantial need exists for a prosthetic spinal disc nucleus formed to facilitate implantation through an annulus opening while providing necessary intradiscal support following implant.

SUMMARY OF THE INVENTION

The invention further relates to an implant for repairing a vertebral disc by providing non-fusion repair of an intervertebral disc by providing a non-osteoinductive, substantially demineralized bone prosthesis that possesses the characteristic of shape memory following implantation. The demineralized bone prosthesis is configured to fit within the space of a spinal disc nucleus and to have sufficient mechanical integrity to provide load bearing in order to act as a cushion between the superior and inferior vertebrae. The invention can be formed from either cortical or cancellous bone and may be processed into an annular, discoid, spheroid, cylindrical spiral, accordion, snake-like and W-shaped cross section.

It is an object of the invention to provide an allograft prosthesis derived from substantially demineralized bone for implantation within a spinal disc nucleus.

It is another object of the invention to provide an allograft cortical bone prosthesis which has been treated to eliminate osteoinductivity.

It is another object of the invention to provide a sterile compressed prosthesis that when hydrated assumes an expanded shape memory.

These and other objects, advantages, and novel features of the present invention will become apparent when considered with the teachings contained in the detailed disclosure along with the accompanying drawings.

DETAILED DESCRIPTION OF THE INVENTION

Figure 2:
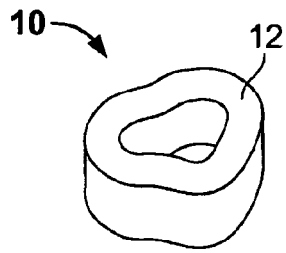
FIG. 2 is a perspective view of a ring shaped spinal disc implant.
Figure 3:
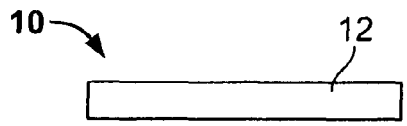
FIG. 3 is a side elevational view of a dehydrated compressed disc implant of FIG. 2 which can be used in the repair of a spinal disc.
Figure 4:
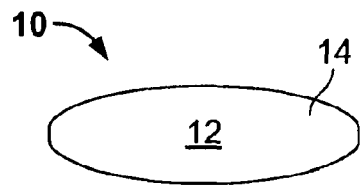
FIG. 4 is a side elevational view of a spinal disc implant of FIG. 3 when hydrated and expanded.

While the present invention is susceptible of embodiment in various forms as is shown in the drawings, and will hereinafter be described, a presently preferred embodiment is set forth with the understanding that the present disclosure is to be considered as an exemplification of the invention, and is not intended to limit the invention to the specific embodiments disclosed herein. The preferred embodiment and best mode of the invention for these purposes is shown in FIGS. 2 through 4.

Figure 1:
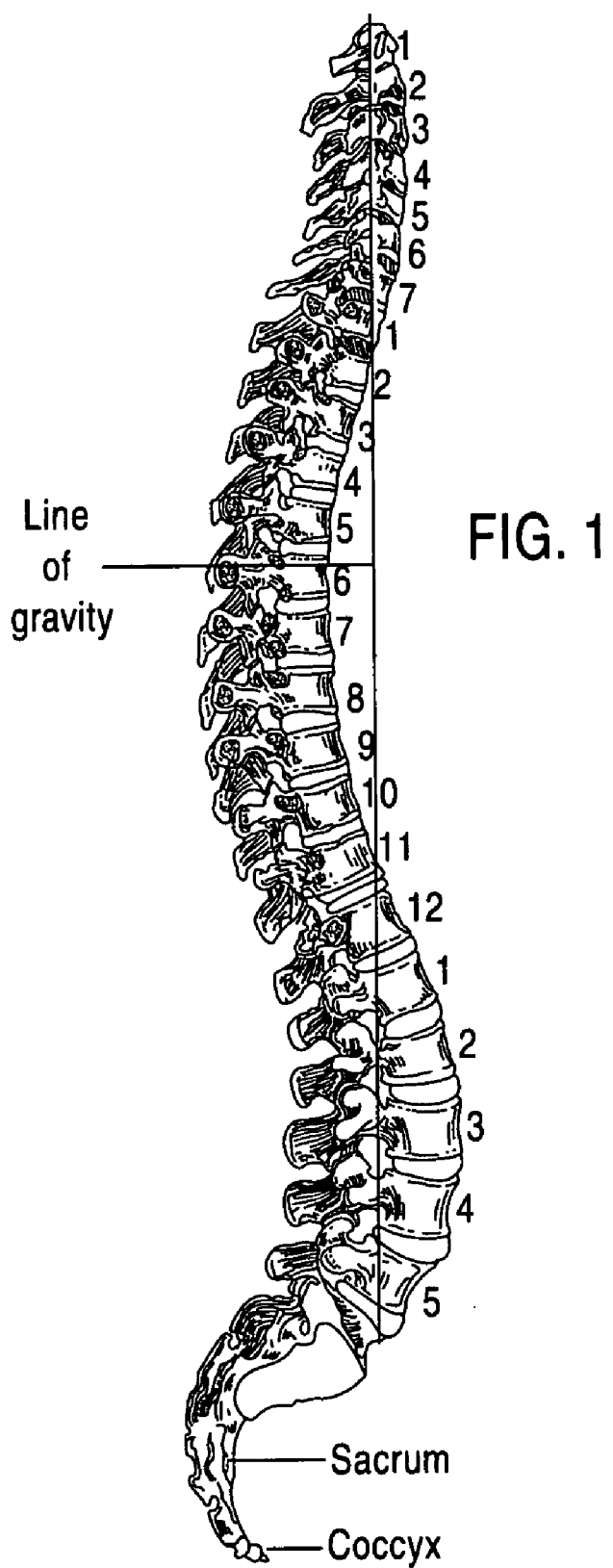
FIG. 1 is a side elevational view of the spinal column with the individual vertebrae being numbered.

The present invention is directed toward a spinal disc repair implant fashioned from demineralized human allograft bone and more particularly toward an implant 10 that includes at least one load bearing elastic body 12 sized for introduction into an intervertebral disc space as shown in FIG. 1. FIG. 1 shows a spinal column with numbered vertebrae separated by discs. The implants have shape memory and are configured to have a specific original shape that allows extensive deformation without permanent deformation, cracks, tears or other breakage in the implant. The original shape of the implant is configured to allow it to be placed into a disc nucleus with minimal disruption to the disc annulus. Following implantation and re-hydration, the implants are designed to return to their original shape within the disc space. The implant body 12 can be surrounded by a resorbable shell that provides the initial fixation for the elastic body within the disc space.

The present invention provides intervertebral disc implants that may fully or partially replace the disc itself, or natural, or native, nucleus pulposus in humans and are configured to resist expulsion or other migration through a defect, or other opening, in the annulus fibrosis and to resist excessive migration within an intervertebral disc space.

The implant 10 is fabricated into the desired shape from a 6-12 mm thick cortical cross-section of long bones, such as a femur, tibia, or humerus. It can also be manufactured from dense cancellous bone for specific uses. The thickness of the cortical walls is at least 2 mm. The cortical walls may also be milled such that they are of uniform or a defined thickness. In one embodiment, the top and bottom faces of the cross-section are milled to have a lordotic curvature that is similar to the native curvature of the superior and inferior vertebral end plates. The total angle of this curvature may be between 3-15 degrees.

The cortical cross sections were demineralized by treating the bone in a dilute acid such as in HCl (0.6N) for at least 48 hours to 96 hours at room temperature to achieve a residual calcium level of about 0.2% wt/wt or less. It is understood that the treatment of the fully demineralized ring shaped cortical tissue (to less than 0.2% residual calcium) can be easily adapted to treatment of other shaped demineralized bone implants. Following demineralization, the resultant tissue is Type I collagen which is tough and resilient with an elastic quality.

After the demineralization step, the bone is either thermally or chemically treated or irradiated to render the tissue non-osteoinductive. Such chemical treatment may include soaking the tissue in a strong oxidizing agent such as 3% hydrogen peroxide for at least 1 hour. Chemical treatment may also involve exposure to a detergent solution that can extract proteins from the bone material such as guanidine hydrochloride, sodium dodecyl sulfate or urea for at least 1 hour. The thermal treatment may involve exposure to heat at temperatures greater than 40° C. for up to 24 hours. Irradiation may involve subjecting the implant to a dosage of at least 20 KiloGrays (Kgy). One gray is defined as an energy absorption of 1 joule per kilogram of irradiated material. One gray is also equivalent to 100 rads. It is a prerequisite that the treatment procedure inactivates or removes the resident bone morphogenic proteins (BMPs) that are known to be contained within bone and have the ability to induce ectopic bone formation. A non-osteoinductive implant is desirable for non fusion spinal disc therapy where motion preservation is the preferred outcome. The chemical, thermal, or radiation treatment aimed to render the bone non-osteoinductive may precede the demineralization process.

Following demineralization, inactivation of osteoinductivity and addition cleaning steps, the pH of the implant is returned to near physiological levels. In the preferred embodiment the pH is restored to a range of 6.6 to 7.4 by soaking the implant in a phosphate-buffered saline solution for at least 30 minutes.

After processing of the implant is complete, the cortical demineralized bone structure is compressed to its desired small configuration preferably so that at least one dimension of the implant is compressed by at least 20% and most preferably where one dimension of the implant is compressed to about 50%. In the preferred embodiment the implant is squeezed radially until opposing sides of the ring shaped structure are brought within close contact of each other, thereby eliminating the hollow center of the bone cross-section. In order to achieve this radial compression without generating fractures in the demineralized bone, the implant may require being axially compressed to first soften its structure in order to allow it to be compressed to the desired smaller configuration. The implant is compressed axially to 20-60% strain in order to render it sufficiently pliable to squeeze radially without causing cracks, tear or other breakage in its structure. After a sufficient amount of water is expelled from the wet collagenous tissue via the axial compression, the structural backbone possesses greater flexibility due to the empty space that had previously been occupied by water molecules at equilibrium. Therefore, the collagen fibers may be further collapsed without inducing fractures in their structure. Once compressed radially, the implant may be held in this shape by placing it into a mold. The compressed implant is then hardened by dehydration. The resulting collapsed ring structure may have a width between 4-12 mm. This smaller compressed shape of the implant allows it to pass through a 4-12 mm small portal in the annulus fibrosus during implantation into the disc nucleus. It is necessary that the size of the annulotomy is kept to these dimension as to not further compromise the integrity of the disc or the ability of the implant to be contained within the disc space.

The implant, having the characteristic of shape-memory expands to its original geometry including the recovery of the height, width and length of its initial shape. If desired, in order to cause rehydration to be more rapid, small perforations are formed in the implant. The holes may be partial, drilled from the axial direction or from the radial direction. The holes should be no greater than 1 mm in diameter. The term DFR, while referring to demineralized femoral ring, can also be interpreted to refer to other demineralized allograft implant shapes. The mechanical compression, which softens the tissue, is what allows the DFRs to be squeezed together without causing fractures in their structure. Without the mechanical compression, the DFRs typically split when compressed radially.

After regaining its annular configuration, the implant serves as a load bearing, flexible prosthesis for the disc nucleus that acts as a malleable cushion between the vertebrae. The ring shaped structure also serves to resist the hoop stresses generated by surrounding annulus fibrosus keeping the annulus under tension. Without providing resistance to these stresses, the fibers of the annulus may separate and weaken leading to further disc degeneration and loss of disc height. By keeping the annulus under tension with an appropriately sized demineralized bone implant design for non fusion disc repair, the integrity of the annulus may be maintained while sparing motion within the spine.

Figure 5:
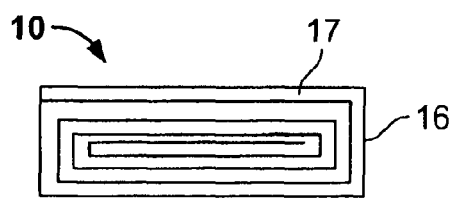
FIG. 5 is a top plan view of another embodiment of the invention disclosing a dehydrated compressed spiral shaped configuration implant embodiment which can be used in the repair of a spinal disc.
Figure 6:
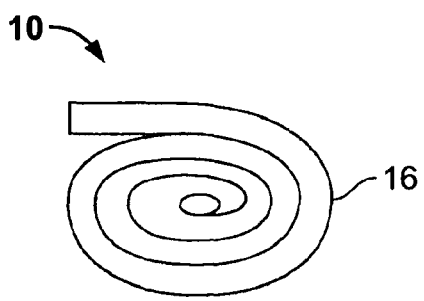
FIG. 6 is a top plan view of the embodiment of FIG. 5 when hydrated.
Figure 7:
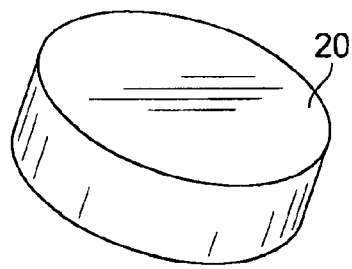
FIG. 7 is an enlarged perspective view of the solid cancellous disc embodiment which can be used in the repair of a spinal disc.
Figure 8:
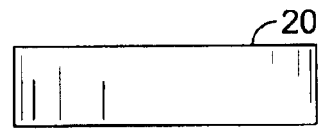
FIG. 8 is a side elevational view of the cancellous disc embodiment of FIG. 7.
Figure 13:
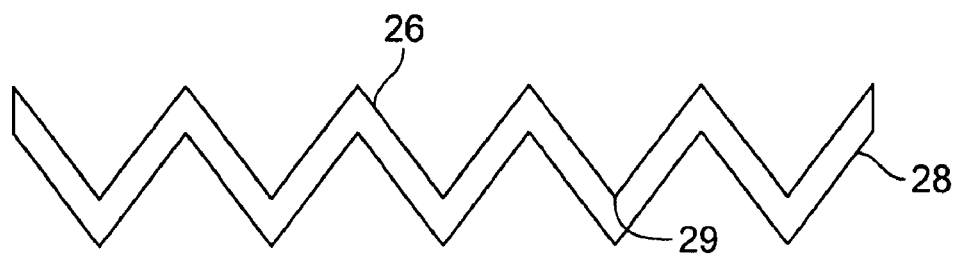
FIG. 13 is an enlarged top plan view of another embodiment of the invention in a hydrated expanded accordion configuration which can be used in the repair of a spinal disc.
Figure 14:
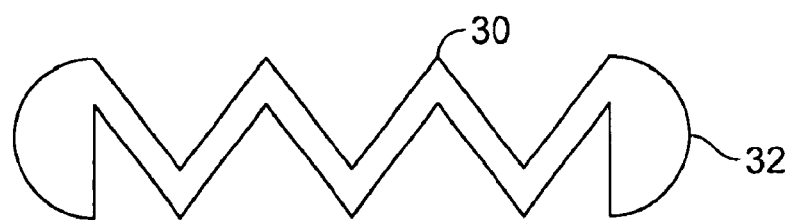
FIG. 14 is an enlarged top plan view of another embodiment of the invention in a hydrated expanded accordion configuration having arcuate ends which can be used in the repair of a spinal disc.
Figure 15:
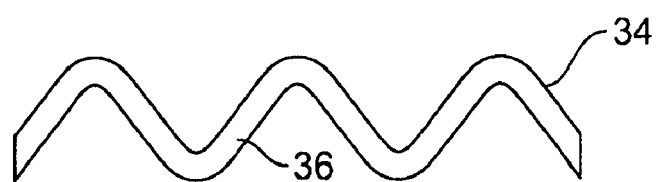
FIG. 15 is an enlarged top plan view of another embodiment of the invention in a hydrated expanded snake-like configuration which can be used in the repair of a spinal disc.
Figure 16:
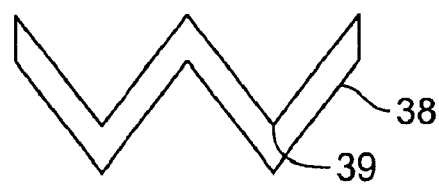
FIG. 16 is an enlarged top plan view of another embodiment of the invention in a hydrated expanded W shape configuration which can be used in the repair of a spinal disc.

The implant 10 has a body 12 with a rounded exterior surface 14 such as that shown in FIGS. 2-4, either ring shaped or of a solid disc shape. A spiral shaped form 16 is cut from a long bone. In this configuration, the bone is cut at an angle circumferentially down the length of a long bone. The height and width of the curved bone strip 17 comprising the spiral may range between 2-8 mm. The spiral form is shown in compressed dehydrated form in FIG. 5 and hydrated form in FIG. 6. The spiral shown in hydrated form in FIG. 6 may be straightened under mechanical force and hardened as shown in FIG. 5. Following implantation and re-hydration, the implant exhibits shape memory regaining its original spiral shape. Other embodiments include the hydrated cancellous form 20 of FIGS. 7 and 8, and the cortical cancellous composite form 22 of FIGS. 9 and 10. In this composite form 22 the cancellous cylinder member 23 is compressed and put into the cortical ring member 24. Additional embodiments are the hydrated T-shaped form 25 of FIG. 11, the hydrated Y-shaped form 27 of FIG. 12, the hydrated accordion form 26 with straight legs 28 of FIG. 13 and a second hydrated accordion form 30 with arcuate ends 32 as shown in FIG. 14. A hydrated snake-like form 34 having a serpentine body is shown in FIG. 15 and a hydrated W-shaped form 38 is shown in FIG. 16 are among the numerous shaped variants which can be used. Folds 29 and 39 of FIGS. 13 and 16 respectively are shown with sharp edges but the same can easily be rounded for specific implant usage.

Additional implant configurations may include solid discoid, cylindrical or rectangular shapes. These demineralized bone forms may be soft ended, folded from any of the described shapes into a second smaller shape that is significantly smaller in at least one dimension, and then placed into a mold. The second smaller shape may be at least 25-50% smaller in at least one dimension after compression or folding. Once fully hydrated, the implant "pops" back to its original configuration and serves as at least one part of a load-bearing flexible disc nucleus augmentation or replacement device.

The implant may also comprise more than a single section of demineralized bone. In one embodiment multiple cross-sections ranging in thickness from 1-6 mm of demineralized cortical bone are layered on top of one another to constitute the disc nucleus implant. This set of bone cross-sections may be designed to have interlocking mechanisms such as dovetail grooves or be milled to have ridges that fit tightly together once fully hydrated. Alternatively, multiple demineralized bone cross-sections may be designed to be fit within each other when hydrated to constitute the nucleus pulposus implant.

Alternatively the spinal disc implants may be manufactured from dense cancellous bone. Sources of dense cancellous bone include distal and proximal femur, distal and proximal tibia, proximal humerus, talus, calcaneus, patella and ilium. Here cancellous bone is demineralized so that it has similar mechanical properties to that of sponge-like material. The resulting highly deformable tissue form may be compressed to a smaller shape that exhibits shape-memory when fully hydrated. It is known that processing time (demineralization, chemical inactivation and restoration of pH) are faster than that for cortical bone, which is denser and less penetrable than highly porous cancellous tissue. In one embodiment a cancellous block is milled into a solid discoid or cylinder shape. The shaped demineralized cancellous bone may then be radially compressed into a tube or axially compressed to resemble a flat sheet. The tissue form may then be hardened in this configuration by dehydration. Upon implantation and rehydration, the cancellous bone expands back to its original configuration and serves as a partial or total disc nucleus replacement device. When hydrated, the demineralized cancellous bone implant serves to act as a cushion between the vertebrae and depending on the degree of expansion from its compressed shape, may also provide a lifting force capable of restoring disc height. The sponge-like characteristics of the demineralized cancellous bone may also allow it to be utilized to soak up fluids at the site of implantation. The porous nature of the demineralized cancellous bone may also allow it to be remodeled more rapidly after implantation than the denser cortical tissue. A plurality of demineralized cancellous bone implants may be used to comprise the disc nucleus implant. In another embodiment, the cancellous bone is configured to have a similar shape to that of a nucleus pulposus with corresponding curvature to that of the native tissue prior to compression into a small shape. This unique shape may be configured to be proportionately sized to be as much as 2-5 times larger than the anatomical void in the disc nucleus. Upon insertion of the implant into a disc, the implant is allowed to expand to its original shape ranging from 50% to 500% greater than its compressed shape.

Figure 9:
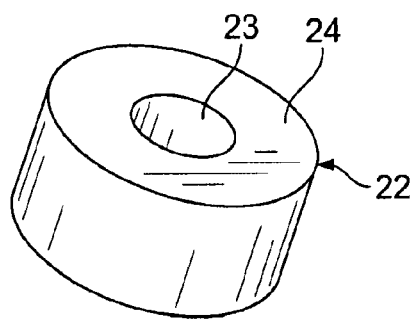
FIG. 9 is an enlarged perspective view of the composite cortical ring with cancellous cylinder placed within the ring embodiment which can be used in the repair of a spinal disc.
Figure 10:
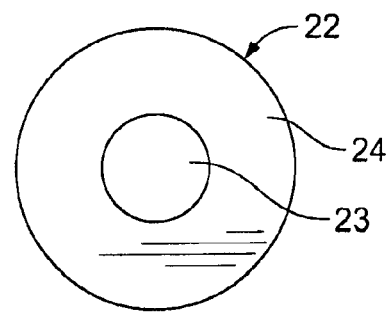
FIG. 10 is a top plan view of the composite cortical cancellous ring of FIG. 9.

In another embodiment as shown in FIGS. 9 and 10, the demineralized bone implant 22 may be fashioned using a combination of cortical and cancellous bone. At least one cylindrical or discoid cancellous block 23 is added to fill the center of a ring-shaped implant 24 derived from cortical bone. The composite implant is compressed to a smaller dimension and then fitted into a mold. Once rehydrated the composite implant regains its original shape.

The demineralized bone implants can be treated with bioactive agents prior to implantation to facilitate biological remodeling of the implant, minimize inflammation or accelerate repair of surrounding tissues. Bioactive molecules include viral particles, plasmids, hormones, antibodies, extracellular matrix proteins, platelet rich plasma or growth factors such as those in TGF-$\beta$, FGF, VEGF, PDGF, EGF, HGF, IGF and Interleuken (IL) families. These molecules may be adsorbed to the surface of the implant, covalently bound to the collagen backbone or impregnated with the bone structure. Growth factors such as TGF-$\beta$ 1, FGF-2 and BMP-7 have been reported in the literature to stimulate regeneration of nucleus pulposus tissue upon injection into a disc space.

The demineralized bone implants may also be treated with one or more types of live cells. Cells may be autologous or allogeneic progenitor cells including but not limited to stroma cells and mesenchymal stem cells. Cells may also be autologous or allogeneic chondrocytes derived from cartilage or disc cells derived from native nucleus pulposus tissue or originate from bone marrow aspirate. Pretreatment of the implants with cells may engender matrix remodeling and tissue regeneration. The combination may be stored frozen before usage or stabilized with cryoprotectants before freezing. Cells may be adhered to the surface of the implant or impregnated within the collagen network. Alternately, autologous cells that were previously recovered, expanded and frozen could be thawed in the operating room and introduced into the implant.

It is also envisioned that a radiopaque marker may be added to the demineralized bone implant in order to make the implant visible during surgery. The radiopaque marker may be derived from beryllium copper, brass, bronze, carbon steel, clad metals, copper, kovar, molybdenum, nickel, niobium, stainless steel, tantalum, titanium, zirconium or other radiopaque material.

If desired anchors may be combined with the implant in order to secure the implant to the superior or inferior vertebra and prevent the implant from migrating from the disc space. The anchoring devices such as sutures tied around the ring-shaped implant which are fastened to suture anchors or bone screws, are then driven into the end plates or through the opposing side of the annulus during implantation in order to preclude implant migration.

Figure 11:
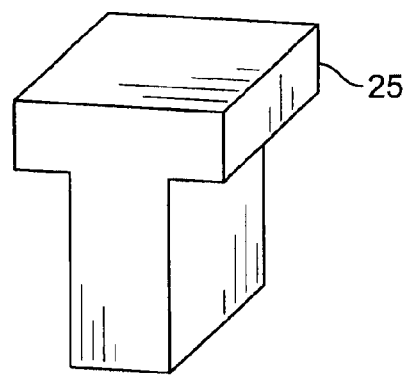
FIG. 11 is an enlarged perspective view of a hydrated T-shaped implant which can be used in the repair of a spinal disc.
Figure 12:
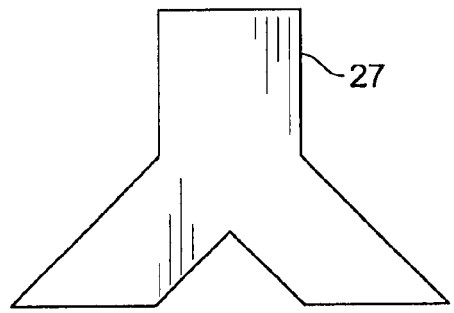
FIG. 12 is an enlarged perspective view of a hydrated Y-shaped implant which can be used in the repair of a spinal disc.

If desired the demineralized bone implant may be used as a plug for insertion into the herniation of the annulus fibrosus to block the potential of re-herniation following a discectomy. As an annulus fibrosus (AF) closure device, the cortical bone base material can have different levels of demineralization and the compressive strength and elasticity may be varied by altering the degree of residual calcium. This may be achieved by varying the time of exposure to acid. The compressive resistance of an intact intervertebral disc is about 2600 Newtons. Various combinations of compressive strength and elasticity can thus be achieved. In one configuration, a ring shaped implant may have an additional plug section milled into one of its sides. Upon insertion into the disc space, the implant is oriented such that the plug is situated into the defect of the annulus fibrosus. In yet another embodiment as shown in FIGS. 11 and 12 the implant may be configured to have a T-shape or a Y-shape where the implant possesses a cylindrical plug section with two folding flaps. Prior to implantation the flaps are folded so that they can pass through a portal in the annulus fibrosus and be secured in the disc. Upon rehydration these flaps return to their initial configuration pressing against the inner annulus of the implanted disc. The flaps may also be further secured to the disc annulus via sutures, tacks or anchors.

The tough collagen (Type I) can be used as a plug for insertion in the herniation of the AF as well as replacement of the NP. The device when hydrated will swell up from the rehydration and securely fill the herniated defect. It can be held in place or in a relative position by a suture applied externally to the AF and device.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What we claim is:

1. An implant for non-fusion repair of a defective vertebral disc which occupies a space between a superior vertebra and an inferior vertebra and which includes an annulus fibrosus having outer and inner walls and a nuclear cavity having a boundary bordered by the inner wall of the annulus fibrosus and by the superior and inferior vertebrae, said implant comprising: an exterior surface and a porous load-bearing body defining said exterior surface and having an original shape selected to at least partially fill the nuclear cavity of the defective vertebral disc, said body being formed from substantially demineralized, non-osteoinductive bone such that said body is deformable from its said original shape into a compressed shape that facilitates the insertion of said body into the nuclear cavity of the defective vertebral disc, said body having shape memory such that it assumes its said original shape in response to its exposure to fluid, said body being sized and shaped such that said exterior surface is engageable with a substantial portion of the boundary of the nuclear cavity of the defective vertebral disc when said body assumes its said original shape after insertion into the nuclear cavity of the defective vertebral disc, and wherein said body includes a first section made of cortical bone and a second section made of cancellous bone.

2. The implant of claim 1, wherein said bone has a calcium content that does not exceed about 0.2% wt/wt.

3. The implant of claim 1, wherein said original shape has at least one dimension that is reduced within a range of from 20% to 50% when said body is deformed into its said compressed shape.

4. The implant of claim 1, wherein said original shape has at least one dimension that is reduced by more than 50% when said body is deformed into its said compressed shape.

5. The implant of claim 1, wherein said body has a ring shape, said body including an annular exterior member and a hollow space within said exterior member, said exterior member collapsing when said body is in its said compressed shape to thereby collapse said hollow space.

6. The implant of claim 1, wherein said first section has a ring shape and wherein said second section is positioned within said first section.

7. The implant of claim 1, wherein said body has a cylindrical shape.

8. The implant of claim 1, wherein said body has a spheroid shape.

9. The implant of claim 1, wherein said body has a spiral shape.

10. The implant of claim 1, wherein said body has an accordion shape.

11. The implant of claim 1, wherein said body has a W shape.

12. The implant of claim 1, wherein said body has a rectangular shape.

13. The implant of claim 1, wherein said body includes at least one bioactive agent.

14. The implant of claim 13, wherein said at least one bioactive agent includes one or more substances taken from a group consisting of growth factors, hormones, viral particles, platelet rich plasma, and naked DNA.

15. The implant of claim 14, wherein said growth factors include TGFβ, FGF, VEGF, PDGF, EGF, HGF, IGF and IL superfamilies.

16. The implant of claim 13, wherein said at least one bioactive agent is adsorbed to said body.

17. The implant of claim 13, wherein said body includes a collagen backbone, said at least one bioactive agent being covalently bonded to said collagen backbone.

18. The implant of claim 13, wherein said body is impregnated with said at least one bioactive agent.

19. The implant of claim 1, wherein said body includes at least one tissue fragment.

20. The implant of claim 1, wherein said body includes bone marrow aspirate.

21. The implant of claim 1, wherein said body includes live cells.

22. The implant of claim 21, wherein said live cells include disc cells.

23. The implant of claim 21, wherein said live cells include marrow cells.

24. The implant of claim 21, wherein said live cells include stroma cells.

25. The implant of claim 21, wherein said live cells include mesenchymal cells.

26. The implant of claim 21, wherein said live cells include chondrocytes.

27. The implant of claim 21, wherein said live cells include autogenic stem cells.

28. The implant of claim 21, wherein said live cells are adhered to a surface of said body.

29. The implant of claim 21, wherein said body includes a collagen network, said collagen network being impregnated with said live cells.

30. The implant of claim 1, wherein said body includes a radiopaque marker.

31. The implant of claim 1, wherein said body includes a top face and a bottom face opposite said top face.

32. The implant of claim 31, wherein said top face of said body has a lordotic curvature that conforms to the curvature of a vertebral end plate of the superior vertebra.

33. The implant of claim 31, wherein said bottom face of said body has a lordotic curvature that conforms to the curvature of a vertebral end plate of the inferior vertebra.

34. The implant of claim 31, wherein said body includes a plurality of holes, each of said holes having a diameter less than 1 mm and extending in an axial direction that is substantially perpendicular to said top face and said bottom face of said body.

35. The implant of claim 31, wherein said body includes a plurality of holes, each of said holes having a diameter less than 1 mm and extending in a radial direction that is substantially parallel to said top face and said bottom face of said body.

36. The implant of claim 1, wherein said body has a pH in range of from 6.6 to 7.4.

37. The implant of claim 1, wherein said body assumes its said original shape in response to its exposure to a physiological fluid.

38. The implant of claim 1, wherein the annulus fibrosus has a major axis and a minor axis, said body being sized and shaped such that said exterior surface is engageable with a substantial portion of the inner wall of the annulus fibrosus along its major and minor axes when said body assumes its said original shape after insertion into the nuclear cavity of the defective vertebral disc, whereby said implant exerts a tensile force on the inner wall of the annulus fibrosus along its major and minor axes to thereby resist hoop stresses generated by the annulus fibrosus.

39. The implant of claim 1, wherein said exterior surface includes a top face and a bottom face, said body being sized and shaped such that said top face of said implant is engageable with a substantial portion of an end plate of the superior vertebra when said body is in its said original shape, and such that said bottom face of said implant is engageable with a substantial portion of an end plate of the inferior vertebra when said body is in its said original shape, whereby said implant inhibits further vertebral disc height collapse when said body is in its said original shape.

40. The implant of claim 1, wherein the annulus fibrosus of the defective vertebral disc includes an opening that extends from its outer wall to its inner wall, said original shape of said body being selected so as to inhibit the expulsion of said implant through the opening in the annulus fibrosus when said body is in its said original shape, whereby said implant is retained within the nuclear cavity of the defective vertebral disc when said body is in its said original shape.

41. The implant of claim 40, wherein said body includes a plug section extending therefrom and having a size and shape selected such that said plug section fits within the opening in the annulus fibrosus upon insertion of said body into the nuclear cavity of the defective vertebral disc.

42. The implant of claim 41, wherein said body has a T shape.

43. The implant of claim 41, wherein said body has a Y shape.

44. The implant of claim 41, wherein said body has a ring shape, said body including an annular exterior member and a hollow space within said exterior member, and said plug section extending radially outwardly from said annular exterior member.

45. The implant of claim 1, wherein said exterior surface of said body has a shape that substantially conforms to the shape of the inner wall of the annulus fibrosus.

* * * * *